United States Patent [19]
Fujii et al.

[11] Patent Number: 5,801,288
[45] Date of Patent: Sep. 1, 1998

[54] DIPHENYL SULFONE DERIVATIVE AND RECORDING MATERIAL PREPARED THEREFROM

[75] Inventors: Hiroshi Fujii, Chiba; Ryuichi Kaneko, Hoya; Shinichi Satoh, Chiba, all of Japan

[73] Assignee: Nippon Soda Co., Ltd., Tokyo, Japan

[21] Appl. No.: 737,911

[22] PCT Filed: Jun. 1, 1995

[86] PCT No.: PCT/JP95/01072

§ 371 Date: Nov. 26, 1996

§ 102(e) Date: Nov. 26, 1996

[87] PCT Pub. No.: WO95/33714

PCT Pub. Date: Dec. 14, 1995

[30] Foreign Application Priority Data

Jun. 6, 1994 [JP] Japan .................................. 6-147146
Apr. 7, 1995 [JP] Japan .................................. 7-108058

[51] Int. Cl.[6] .................................................. C07C 317/14
[52] U.S. Cl. ........................... 568/33; 568/32; 568/45; 430/399
[58] Field of Search ................................ 568/32, 33, 45; 430/399

[56] References Cited

PUBLICATIONS

American Heritage Dictionary –definition of chromogen, p. 341, 1992.

*Primary Examiner*—C. Warren Ivy
*Assistant Examiner*—Jean F. Vollano
*Attorney, Agent, or Firm*—Joseph C. Mason, Jr.

[57] ABSTRACT

The present invention is directed to recording materials characterized in that the recording materials comprise at least one of diphenyl sulfone derivatives represented by the following general formula (I);

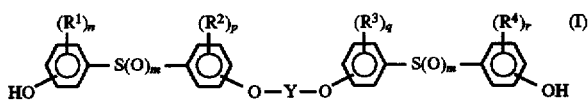

wherein Y represents a linear or branched (un)-saturated $C_1$–$C_{12}$ hydrocarbon group, a $C_1$–$C_8$ hydrocarbon group having an ether linkage, or a group represented by a general formula;

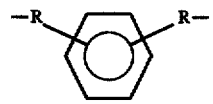

wherein R represents methylene or ethylene; $R^1$, $R^2$, $R^3$ and $R^4$ represent each independently lower alkyl or lower alkenyl; m represents 0 or an integer of 1 or 2,; and n, p, q and r represent each independently 0 or an integer of 1 to 4, provided when n, p, q and r are each 2 or above, the substituents represented by $R^1$, $R^2$, $R^3$ and $R^4$ may be each different from one another.

2 Claims, No Drawings

DIPHENYL SULFONE DERIVATIVE AND RECORDING MATERIAL PREPARED THEREFROM

FIELD OF THE INVENTION

The present invention relates to recording materials comprising at least one novel diphenyl sulfone derivative and having improved the preservability of colored-images developed therefrom.

formula as an image-stabilizing agent in Japanese patent laid-opened No. Hei 5-194368.

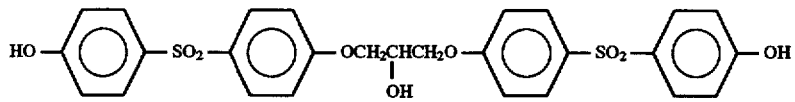

BACKGROUND ART

Recording materials based on color-forming reaction of a coloring chromogen and a developer have been widely used for thermal recording papers to be utilized for output recording by facsimile, printers, etc., or for carbonless papers to be utilized for accounting cards for producing several copies at once, since those recording materials enable to make recording in short time by using relatively simple apparatuses without requiring complex recording procedure, such as developing, fixing, etc.

For such a recording material, the one which can develop color immediately, prevent color change in non-image area (hereinafter referred to as background) and provide high preservability to colored-images and background, have been required. Further, in recent years, such recording materials have been used in a great amount especially in the field of label printing where reliability to recorded-images being highly respected. In addition, recording materials that can provide colored-images having high preservability and resistance against plasticizers and oils, which are contained in organic high molecular materials being used for packages, have been strongly required. For such purpose, investigation from various points of view to find efficient auxiliary agents such as stabilizers as well as color-forming chromogens and color developers have been carried out. However, such materials having sufficient properties as described above have not been found yet.

For the examples of compounds similar to the compound specified in the present invention, various diphenyl sulfone derivatives, phenethyl alcohol derivatives and the like can be exemplified. These compounds are known as a color developer to be used for recording materials. Diphenyl sulfone derivatives having either alkoxyl or aralkyloxyl group at one side and hydroxyl group at the other side are disclosed in Japanese patent laid-opened Nos. Sho 57-210886, Sho 58-20493, Sho 58-82788, Sho 58-132593, Sho 60-13852, World opened No. WO84/02882, etc. respectively.

More recently, some patent applications for aiming at improving the preservability of recording materials as described above have disclosed recording materials containing epoxyl group, such as novolac-type epoxy resins and glycidyl compounds. The applicant of the present invention has also filed a patent wherein a compound of 4-hydroxy-4'-(2-methylglycidyloxy)diphenyl sulfone is specified for the same object. However, all of those compounds have not been capable of providing enough preservability to developed-images.

Furthermore, the applicant of the present invention has disclosed a compound represented by the following general However, the compound mentioned hereinabove has been found as having inferior property in resistance to moisture and heat, and it can give only less density to developed-color and less sensitivity, when it is used as a color developer.

As described above, in recent years, the improvement in recording materials for aiming at securing preservability for colored-images, especially resistance to plasticizers and oils, are highly required. Therefore, it is an object of the present invention to provide recording materials which can give excellent preservability for colored-images, enough color density when it is developed, and excellent property for preventing color change in the background.

DISCLOSURE OF THE INVENTION

The present invention relates to recording materials comprising at least one of diphenyl sulfone derivatives represented by the following general formula (I);

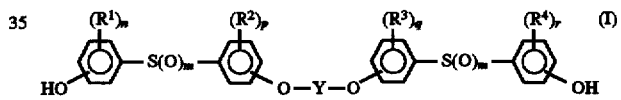

wherein Y represents a linear or branched (un)-saturated $C_1$–$C_{12}$ hydrocarbon group, a $C_1$–$C_8$ hydrocarbon group having an ether linkage, or a group represented by the following general formula;

wherein R represents methylene or ethylene; $R^1$, $R^2$, $R^3$ and $R^4$ are each independently represent lower alkyl or lower alkenyl; m represents 0 or an integer of 1 or 2; and n, p, q and r each independently represent 0 or an integer of 1 to 4, provided when n, p, q and r are each 2 or above, the substituents represented by $R^1$, $R^2$, $R^3$ and $R^4$ may be each different from one another.

For the concrete examples of Y, methylene, ethylene, trimethylene, tetramethylene, pentamethylene, hexamethylene, heptamethylene, octamethylene, nonamethylene, decamethylene, undecamethylene, dodecamethylene, methyl methylene, dimethyl methylene, methyl ethylene, methylene ethylene, ethyl ethylene, 1,2-dimethyl ethylene, 1-methyl trimethylene, 1-methyl tetramethylene, 1,3-dimethyl trimethylene, 1-ethyl-4-methyl-tetramethylene, vinylene, propenylene, 2-butenylene, ethynylene, 2-butynylene, 1-vinyl ethylene, ethylene oxyethylene, tetramethylene oxytetramethylene, ethylene oxyethylene oxyethylene, ethylene oxymethylene oxyethylene, 1,3-dioxane-5,5-bismethylene, 1,2-xylyl, 1,3-xylyl, 1,4-xylyl and the like can be exemplified.

The lower alkyls and lower alkenyls represented by $R^1$, $R^2$, $R^3$ and $R^4$ are each independently any of $C_1$–$C_6$ alkyls or $C_2$–$C_4$ alkenyls, and for the concrete examples thereof, methyl, ethyl, n-propyl, isopropyl, n-butyl, sec-butyl, tert-butyl, n-pentyl, isopentyl, neopentyl, tert-pentyl, n-hexyl, isohexyl, 1-methylpentyl, 2-methylpentyl, vinyl, allyl, isopropenyl, 1-propenyl, 2-butenyl, 3-butenyl, 1,3-butadienyl, 2-methyl-2-propenyl or the like can be exemplified.

Among the compounds represented by the general formula (I), it is preferable to use diphenyl sulfone derivatives represented by the following general formula (II).

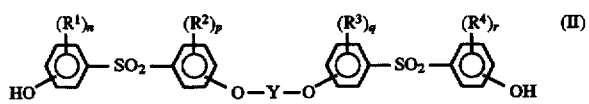

Particularly, it is preferable to use compounds represented by the following general formula (III).

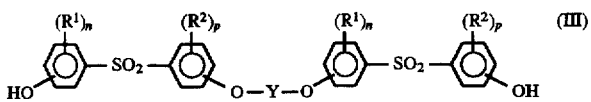

Further, from the viewpoint of chemical synthesis, compounds represented by the following general formula (IV) are more advantageous.

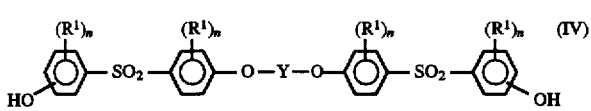

In the following Tables 1 to 4, the concrete examples of diphenyl sulfone derivatives represented by the general formula (II) are recited, however, the compounds according to the present invention shall not be limited to the following examples. It should be noted that all of possible isomers for the recited-derivatives are also fallen within the scope of the compounds specified in the present invention.

TABLE 1

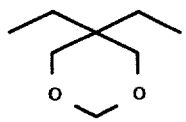

| Compound No. | $(R^1)n$ | $(R^2)p$ | $(R^3)q$ | $(R^4)r$ | Y | Melting Point(°C.) |
|---|---|---|---|---|---|---|
| 1-1 | — | — | — | — | $-CH_2-$ | 213–215 |
| 1-2 | — | — | — | — | $-(CH_2)_2-$ | 263–267 |
| 1-3 | — | — | — | — | $-(CH_2)_3-$ | |
| 1-4 | — | — | — | — | $-(CH_2)_4-$ | 209–213 |
| 1-5 | — | — | — | — | $-(CH_2)_5-$ | |
| 1-6 | — | — | — | — | $-(CH_2)_6-$ | 225–226 |
| 1-7 | — | — | — | — | $-(CH_2)_7-$ | |
| 1-8 | — | — | — | — | $-(CH_2)_8-$ | |
| 1-9 | — | — | — | — | $-(CH_2)_9-$ | |
| 1-10 | — | — | — | — | $-(CH_2)_{10}-$ | |
| 1-11 | — | — | — | — | $-(CH_2)_{11}-$ | |
| 1-12 | — | — | — | — | $-(CH_2)_{12}-$ | 92–96 |
| 1-13 | — | — | — | — | $-CH(CH_3)-$ | |
| 1-14 | — | — | — | — | $-C(CH_3)_2-$ | |
| 1-15 | — | — | — | — | $-CH(CH_3)CH_2-$ | |
| 1-16 | — | — | — | — | $-CH_2C(=CH_2)-$ | |
| 1-17 | — | — | — | — | $-CH(CH_2CH_3)CH_2-$ | |
| 1-18 | — | — | — | — | $-CH(CH_3)CH(CH_3)-$ | |
| 1-19 | — | — | — | — | $-CH(CH_3)CH_2CH_2-$ | 94–98 |
| 1-20 | — | — | — | — | $-CH(CH_3)(CH_2)_3-$ | |
| 1-21 | — | — | — | — | $-CH(CH_3)CH_2CH(CH_3)-$ | |
| 1-22 | — | — | — | — | $-CH(CH_3)(CH_2)_2CH(CH_2CH_3)-$ | |
| 1-23 | — | — | — | — | $-CH=CH-$ | |
| 1-24 | — | — | — | — | $-CH=CHCH_2-$ | |
| 1-25 | — | — | — | — | $-CH_2CH=CHCH_2-$ | 205–209 |
| 1-26 | — | — | — | — | $-C\equiv C-$ | |
| 1-27 | — | — | — | — | $-CH_2C\equiv CCH_2-$ | 147–148 |
| 1-28 | — | — | — | — | $-CH(CH=CH_2)CH_2-$ | 215–216 |
| 1-29 | — | — | — | — | (see structure) | |
| 1-30 | — | — | — | — | $-(CH_2)_2O(CH_2)_2-$ | 171–172 |
| 1-31 | — | — | — | — | $-(CH_2)_4O(CH_2)_4-$ | |
| 1-32 | — | — | — | — | $-(CH_2)_2O(CH_2)_2O(CH_2)_2-$ | 122–125 |
| 1-33 | — | — | — | — | $-(CH_2)_2OCH_2O(CH_2)_2-$ | 112–113 |

TABLE 1-continued $$\text{HO} - \underset{(R^1)n}{\bigcirc} - SO_2 - \underset{(R^2)p}{\bigcirc} - O - Y - O - \underset{(R^3)q}{\bigcirc} - SO_2 - \underset{(R^4)r}{\bigcirc} - OH$$

| Compound No. | $(R^1)n$ | $(R^2)p$ | $(R^3)q$ | $(R^4)r$ | Y | Melting Point(°C.) |
|---|---|---|---|---|---|---|
| 1-34 | — | — | — | — | $-H_2C-\text{C}_6H_4-CH_2-$ (para) | 220–222 |
| 1-35 | — | — | — | — | $-H_2C-\text{C}_6H_4-CH_2-$ (ortho) | 159–162 |
| 1-36 | — | — | — | — | $-H_2C-\text{C}_6H_4-CH_2-$ (meta) | 166–167 |
| 1-37 | 3,5-(CH$_3$)$_2$ | 3,5-(CH$_3$)$_2$ | 3,5-(CH$_3$)$_2$ | 3,5-(CH$_3$)$_2$ | $-CH_2-$ | |
| 1-38 | 3,5-(CH$_3$)$_2$ | 3,5-(CH$_3$)$_2$ | 3,5-(CH$_3$)$_2$ | 3,5-(CH$_3$)$_2$ | $-(CH_2)_2-$ | |
| 1-39 | 3,5-(CH$_3$)$_2$ | 3,5-(CH$_3$)$_2$ | 3,5-(CH$_3$)$_2$ | 3,5-(CH$_3$)$_2$ | $-(CH_2)_3-$ | |
| 1-40 | 3,5-(CH$_3$)$_2$ | 3,5-(CH$_3$)$_2$ | 3,5-(CH$_3$)$_2$ | 3,5-(CH$_3$)$_2$ | $-(CH_2)_4-$ | |
| 1-41 | 3,5-(CH$_3$)$_2$ | 3,5-(CH$_3$)$_2$ | 3,5-(CH$_3$)$_2$ | 3,5-(CH$_3$)$_2$ | $-(CH_2)_5-$ | |
| 1-42 | 3,5-(CH$_3$)$_2$ | 3,5-(CH$_3$)$_2$ | 3,5-(CH$_3$)$_2$ | 3,5-(CH$_3$)$_2$ | $-(CH_2)_6-$ | |
| 1-43 | 3,5-(CH$_3$)$_2$ | 3,5-(CH$_3$)$_2$ | 3,5-(CH$_3$)$_2$ | 3,5-(CH$_3$)$_2$ | $-CH(CH_3)CH_2CH_2-$ | |
| 1-44 | 3,5-(CH$_3$)$_2$ | 3,5-(CH$_3$)$_2$ | 3,5-(CH$_3$)$_2$ | 3,5-(CH$_3$)$_2$ | $-CH_2CH=CHCH_2-$ | 245–247 |
| 1-45 | 3,5-(CH$_3$)$_2$ | 3,5-(CH$_3$)$_2$ | 3,5-(CH$_3$)$_2$ | 3,5-(CH$_3$)$_2$ | $-CH(CH=CH_2)CH_2-$ | |
| 1-46 | 3,5-(CH$_3$)$_2$ | 3,5-(CH$_3$)$_2$ | 3,5-(CH$_3$)$_2$ | 3,5-(CH$_3$)$_2$ | $-(CH_2)_2O(CH_2)_2-$ | |
| 1-47 | 3,5-(CH$_3$)$_2$ | 3,5-(CH$_3$)$_2$ | 3,5-(CH$_3$)$_2$ | 3,5-(CH$_3$)$_2$ | $-H_2C-\text{C}_6H_4-CH_2-$ (ortho) | |
| 1-48 | 3,5-(CH$_3$)$_2$ | 3,5-(CH$_3$)$_2$ | 3,5-(CH$_3$)$_2$ | 3,5-(CH$_3$)$_2$ | $-H_2C-\text{C}_6H_4-CH_2-$ (meta) | |
| 1-49 | 3-CH$_2$-CH=CH$_2$ | 3-CH$_2$-CH=CH$_2$ | 3-CH$_2$-CH=CH$_2$ | 3-CH$_2$-CH=CH$_2$ | $-CH_2-$ | |
| 1-50 | 3-CH$_2$-CH=CH$_2$ | 3-CH$_2$-CH=CH$_2$ | 3-CH$_2$-CH=CH$_2$ | 3-CH$_2$-CH=CH$_2$ | $-(CH_2)_2-$ | |
| 1-51 | 3-CH$_2$-CH=CH$_2$ | 3-CH$_2$-CH=CH$_2$ | 3-CH$_2$-CH=CH$_2$ | 3-CH$_2$-CH=CH$_2$ | $-(CH_2)_3-$ | |
| 1-52 | 3-CH$_2$-CH=CH$_2$ | 3-CH$_2$-CH=CH$_2$ | 3-CH$_2$-CH=CH$_2$ | 3-CH$_2$-CH=CH$_2$ | $-(CH_2)_4-$ | |
| 1-53 | 3-CH$_2$-CH=CH$_2$ | 3-CH$_2$-CH=CH$_2$ | 3-CH$_2$-CH=CH$_2$ | 3-CH$_2$-CH=CH$_2$ | $-(CH_2)_5-$ | |
| 1-54 | 3-CH$_2$-CH=CH$_2$ | 3-CH$_2$-CH=CH$_2$ | 3-CH$_2$-CH=CH2. | 3-CH$_2$-CH=CH$_2$ | $-(CH_2)_6-$ | |
| 1-55 | 3-CH$_2$-CH=CH$_2$ | 3-CH$_2$-CH=CH$_2$ | 3-CH$_2$-CH=CH$_2$ | 3-CH$_2$-CH=CH$_2$ | $-CH(CH_3)CH_2CH_2-$ | |
| 1-56 | 3-CH$_2$-CH=CH$_2$ | 3-CH$_2$-CH=CH$_2$ | 3-CH$_2$-CH=CH$_2$ | 3-CH$_2$-CH=CH$_2$ | $-CH_2CH=CHCH_2-$ | 167–172 |
| 1-57 | 3-CH$_2$-CH=CH$_2$ | 3-CH$_2$-CH=CH$_2$ | 3-CH$_2$-CH=CH$_2$ | 3-CH$_2$-CH=CH$_2$ | $-CH(CH=CH_2)CH_2-$ | |
| 1-58 | 3-CH$_2$-CH=CH$_2$ | 3-CH$_2$-CH=CH$_2$ | 3-CH$_2$-CH=CH$_2$ | 3-CH$_2$-CH=CH$_2$ | $-(CH_2)_2O(CH_2)_2-$ | |
| 1-59 | 3-CH$_2$-CH=CH$_2$ | 3-CH$_2$-CH=CH$_2$ | 3-CH$_2$-CH=CH$_2$ | 3-CH$_2$-CH=CH$_2$ | $-H_2C-\text{C}_6H_4-CH_2-$ (ortho) | |

TABLE 1-continued

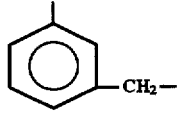

| Compound No. | (R¹)n | (R²)p | (R³)q | (R⁴)r | Y | Melting Point(°C.) |
|---|---|---|---|---|---|---|
| 1-60 | 3-CH₂—CH=CH₂ | 3-CH₂—CH=CH₂ | 3-CH₂—CH=CH₂ | 3-CH₂—CH=CH₂ | 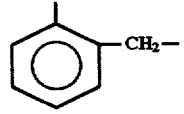 | |
| 1-61 | 3-CH₂—CH=CH₂ | — | — | 3-CH₂—CH=CH₂ | —CH₂— | |
| 1-62 | 3-CH₂—CH=CH₂ | — | — | 3-CH₂—CH=CH₂ | —(CH₂)₂— | |
| 1-63 | 3-CH₂—CH=CH₂ | — | — | 3-CH₂—CH=CH₂ | —(CH₂)₃— | |
| 1-64 | 3-CH₂—CH=CH₂ | — | — | 3-CH₂—CH=CH₂ | —(CH₂)₄— | |
| 1-65 | 3-CH₂—CH=CH₂ | — | — | 3-CH₂—CH=CH₂ | —(CH₂)₅— | |
| 1-66 | 3-CH₂—CH=CH₂ | — | — | 3-CH₂—CH=CH₂ | —(CH₂)₆— | |
| 1-67 | 3-CH₂—CH=CH₂ | — | — | 3-CH₂—CH=CH₂ | —CH(CH₃)CH₂CH₂— | |
| 1-68 | 3-CH₂—CH=CH₂ | — | — | 3-CH₂—CH=CH₂ | —CH₂CH=CHCH₂— | |
| 1-69 | 3-CH₂—CH=CH₂ | — | — | 3-CH₂—CH=CH₂ | —CH(CH=CH₂)CH₂— | |
| 1-70 | 3-CH₂—CH=CH₂ | — | — | 3-CH₂—CH=CH₂ | —(CH₂)₂O(CH₂)₂— | |
| 1-71 | 3-CH₂—CH=CH₂ | — | — | 3-CH₂—CH=CH₂ | 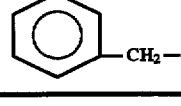 | |
| 1-72 | 3-CH₂—CH=CH₂ | — | — | 3-CH₂—CH=CH₂ | | |

TABLE 2

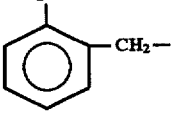

| Compound No. | (R¹)n | (R²)p | (R³)q | (R⁴)r | Y | Melting Point(°C.) |
|---|---|---|---|---|---|---|
| 2-1 | — | — | — | — | —CH₂— | |
| 2-2 | — | — | — | — | —(CH₂)₂— | |
| 2-3 | — | — | — | — | —(CH₂)₃— | |
| 2-4 | — | — | — | — | —(CH₂)₄— | |
| 2-5 | — | — | — | — | —(CH₂)₅— | |
| 2-6 | — | — | — | — | —(CH₂)₆— | |
| 2-7 | — | — | — | — | —CH(CH₃)CH₂CH₂— | |
| 2-8 | — | — | — | — | —CH₂CH=CHCH₂— | |
| 2-9 | — | — | — | — | —CH(CH=CH₂)CH₂— | |
| 2-10 | — | — | — | — | —(CH₂)₂O(CH₂)₂— | |
| 2-11 | — | — | — | — | | |

TABLE 2-continued
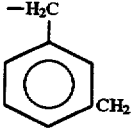
| Compound No. | (R¹)n | (R²)p | (R³)q | (R⁴)r | Y | Melting Point(°C.) |
|---|---|---|---|---|---|---|
| 2-12 | — | — | — | — | —H₂C—C₆H₄—CH₂— | |
TABLE 3
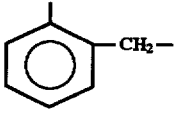
| Compound No. | (R¹)n | (R²)p | (R³)q | (R⁴)r | Y | Melting Point(°C.) |
|---|---|---|---|---|---|---|
| 3-1 | — | — | — | — | —CH₂— | |
| 3-2 | — | — | — | — | —(CH₂)₂— | |
| 3-3 | — | — | — | — | —(CH₂)₃— | |
| 3-4 | — | — | — | — | —(CH₂)₄— | |
| 3-5 | — | — | — | — | —(CH₂)₅— | |
| 3-6 | — | — | — | — | —(CH₂)₆— | |
| 3-7 | — | — | — | — | —CH(CH₃)CH₂CH₂— | |
| 3-8 | — | — | — | — | —CH₂CH=CHCH₂— | |
| 3-9 | — | — | — | — | —CH(CH=CH₂)CH₂— | |
| 3-10 | — | — | — | — | —(CH₂)₂O(CH₂)₂— | |
| 3-11 | — | — | — | — | —H₂C—(o-C₆H₄)—CH₂— | |
| 3-12 | — | — | — | — | —H₂C—(m-C₆H₄)—CH₂— | |

TABLE 4

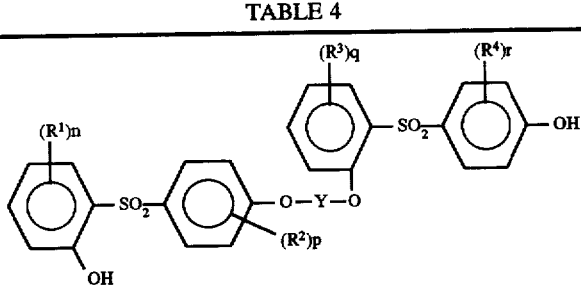

| Compound No. | $(R^1)n$ | $(R^2)p$ | $(R^3)q$ | $(R^4)r$ | Y | Melting Point(°C.) |
|---|---|---|---|---|---|---|
| 4-1 | — | — | — | — | $-CH_2-$ | |
| 4-2 | — | — | — | — | $-(CH_2)_2-$ | |
| 4-3 | — | — | — | — | $-(CH_2)_3-$ | |
| 4-4 | — | — | — | — | $-(CH_2)_4-$ | |
| 4-5 | — | — | — | — | $-(CH_2)_5-$ | |
| 4-6 | — | — | — | — | $-(CH_2)_6-$ | |
| 4-7 | — | — | — | — | $-CH(CH_3)CH_2CH_2-$ | |
| 4-8 | — | — | — | — | $-CH_2CH=CHCH_2-$ | |
| 4-9 | — | — | — | — | $-CH(CH=CH_2)CH_2-$ | |
| 4-10 | — | — | — | — | $-(CH_2)_2O(CH_2)_2-$ | |
| 4-11 | — | — | — | — | $-H_2C-\text{(o-C}_6\text{H}_4\text{)}-CH_2-$ | |
| 4-12 | — | — | — | — | $-H_2C-\text{(m-C}_6\text{H}_4\text{)}-CH_2-$ | |

As the method for preparing the diphenyl sulfone derivatives represented by the general formula (I), it is preferable to carry out either in water or in bilayer solvent system composed of water and an organic solvent in the presence of a basic substance, and the said derivatives, for example, can be prepared in accordance with the following reaction formula. For the starting materials, it is preferable to use either of 4,4'-dihydroxydiphenyl sulfone derivative or 2,4'-dihydroxydiphenyl sulfone derivative, as those can be easily obtained commercially.

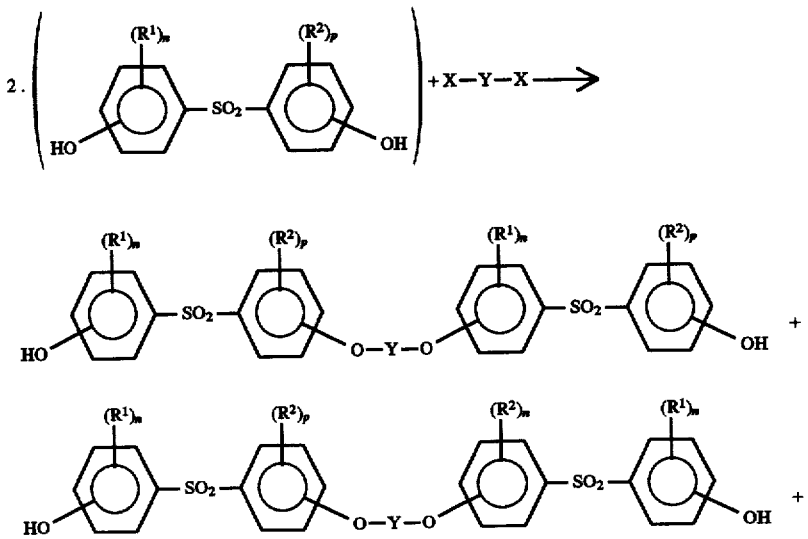

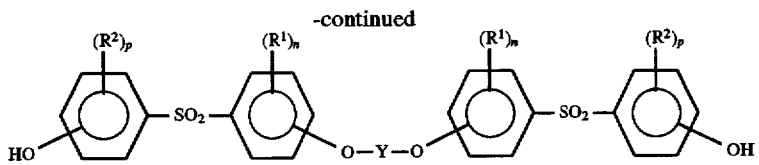

Wherein, X represents halogen, such as chlorine and bromine, and other substituents in the reaction formula above are as described above.

In the bilayer solvent system comprising water and an organic solvent, the reaction is taken place in a water-insoluble organic solvent, for examples, benzene-type organic solvent, such as benzene, toluene, chlorobenzene and dichlorobenzene; ketone-type organic solvent, such as diethyl ketone and methyl isobutyl ketone; and ester-type organic solvent, such as ethyl acetate, for several hours to several ten hours at a temperature of from 60° to 90° C. in the presence of an alkaline substance, for examples, a hydroxide of either alkali metals or alkaline earth metals, more particularly sodium hydroxide, potassium hydroxide or lithium hydroxide.

In the water solvent system mentioned above, the reaction is taken place in water during several hours to several ten hours at a temperature of from 0° to 90° C. in the presence of the alkaline substance described above.

After the reaction, single highly-purified compound can be obtained following to a process of selective extraction with a solvent.

The compounds according to the present invention can be utilized for any uses insofar as the recording materials being based on coloring chromogens concern, for examples, for thermal recording papers, carbonless papers and the like.

The recording material according to the present invention can achieve the object of the present invention if one or more of the compounds specified in the present invention are contained in the recording material comprising a coloring chromogen. Therefore, the compounds of the present invention can be also used as a stabilizing agent for colored-images having resistance to plasticizers as well as a developer provided with excellent resistance to plasticizers. Such characteristic having both functions as a developer and a stabilizing agent for colored-images gives a great advantage, since it can reduce a comparative use rate required for a developer and an image-stabilizing agent in total relative to a rate of a coloring chromogen, which thus leading to less production cost of the recording materials.

As a method for preparing the recording material containing a coloring chromogen, any methods which have been generally employed can be used. For the example, the recording material can be prepared by combining the inventive compound with a developer and auxiliary agents, such as a sensitizer, when the material is used as a image-stabilizing agent, and with certain auxiliary agent, such as a sensitizer, when it is used as a developer. Naturally, several of the compounds of the present invention can be used in combination as an image-stabilizing agent on the one hand, and as a developer on the other hand. Also, by jointly using a compound of which use being identical to that of the compounds of the present invention, it is possible to prepare the recording materials to which a characteristic coloring property be given.

When utilizing the compounds of the present invention for thermal recording papers, those can be used in the same manner as the ones for using known developers and image-stabilizing agents. For the example, the compound of the present invention is dispersed into aqueous solution of water-soluble binder together with auxiliary agents and coloring dyes, and the resultant suspension is then mixed, applied to a supporting material, such as papers, and subsequently dried.

Furthermore, in addition to the method as described above to contain the compound in the color-forming layer, it is also possible to combine the compound into any layer of protecting layer, under-coating layer or what layer else, in case said color-forming layer being composed of multiple-layers structure.

The use rate of the compound of the present invention relative to a coloring chromogen shall be 0.1 to 5 parts by weight, and preferably from 0.2 to 2 parts by weight, based on 1 part by weight of the coloring chromogen when it is used as an image-stabilizing agent, while the said rate shall be 1 to 10 parts by weight, and preferably from 1.5 to 5 parts by weight, based on 1 part by weigh of the coloring chromogen when it is used as a developer.

As the auxiliary agents as described above, image-stabilizing agents, sensitizers, fillers, dispersing agents, antioxidants, desensitizers, antitack agents, defoamers, light-stabilizing agents, fluorescent brightening agents and the like can be added if appropriate.

The selection of sensitizer can be made optionally, and for the examples thereof, higher fatty acid amides, such as amide stearate, benzamide, anilide stearate, anilide acetoacetate, thioacetoanilide, dibenzyl oxalate, di-(4-methylbenzyl) oxalate, di-(4-chlorobenzyl) oxalate, dimethyl phthalate, dimethyl terephthalate, dibenzyl terephthalate, dibenzyl isophthalate, bis(tert-butylphenol) and its derivatives, diethers of 4,4'-dihydroxydiphenyl sulfone, 1,2-bis(phenoxy)ethane, 1,2-bis(4-methylphenoxy) ethane, 1,2-bis(3-methylphenoxy)ethane, 2-naphthyl benzyl ether, diphenyl amine, carbazole, 2,3-di-m-tolylbutane, 4-benzylbiphenyl, 4,4'-dimethylbiphenyl, m-terphenyl, di-β-naphthylphenylenediamine, phenyl 1-hydroxyl naphthoate, 2-naphthyl benzyl ether, 4-methylphenyl biphenyl ether, 2,2-bis(3,4-dimethylphenyl)ethane, 2,3,5,6-tetramethyl-4'-methyldiphenyl methane and the like can be exemplified.

For the examples of the filler, clay, talc, kaolin, satin white, titanium oxide, calcium carbonate, magnesium carbonate, barium sulfate, magnesium silicate, aluminium silicate and the like can be exemplified.

For the examples of the dispersing agents, esters of sulfosuccinic acid, such as dioctyl sodium sulfosuccinate, sodium salts and fatty acid salts of sulfate esters of lauryl alcohol and the like can be given.

For the examples of the image-stabilizing agents, diphenyl sulfones containing epoxyl group, such as 4-benzyloxy-4'-(2-methylglycidyloxy) diphenyl sulfone and 4,4'-diglycidyloxydiphenyl sulfone, 1,4-diglycidyloxybenzene, 4-(α-(hydroxymethyl)-benzyloxy)-4'-hydroxydiphenyl sulfone, 2-propanol derivatives, salicylic acid derivatives, metal salts (particularly zinc salt) of oxynaphthoic acid derivatives, and other water-insoluble zinc compounds, can be exemplified.

For the examples of the antioxidants, 2,2'-methylene-bis (4-methyl-6-tert-butylphenol), 2,2'-methylene-bis(4-ethyl- 6-tert-butylphenol), 4,4'-propylmethylene-bis(3-methyl-6-tert-butylphenol), 4,4'-butylidene-bis(3-methyl-6-tert-butylphenol), 4,4'-thio-bis(2-tert-butyl-5-methylphenol), 1,1,3-tris(2-methyl-4-hydroxy-5-tert-butylphenyl), butane, 1,1,3-tris(2-methyl-4-hydroxy-5-cyclohexyphenyl)butane and the like, and for the examples of the desensitizers, aliphatic higher alcohols, polyethylene glycol, guanidine derivatives and the like, can be exemplified, respectively.

Further, for the examples of the antitack agent, stearic acid, zinc stearate, calcium stearate, carnauba wax, paraffin wax, wax ester and the like can be exemplified.

And, for the examples of the light-stabilizing agents, salicylic acid-type ultraviolet radiation absorbing agents, benzoic acid-type ultraviolet radiation absorbing agents, benzotriazole-type ultraviolet radiation absorbing agents, cyanoacrylate-type ultraviolet radiation absorbing agents, hindered amine-type ultraviolet radiation absorbing agents and the like can be exemplified.

As the coloring chromogen to be used together with the compounds according to the present invention, leuco chromogens comprising any of fluoran, phthalide, lactam, triphenyl methane, phenothiazine and spiropyran compounds can be used. However, the coloring chromogen shall not be limited to the ones described above in the present invention, and any coloring chromogens which develop color when those have contacted with a developer of acidic substance can be used without limitation.

Among the coloring chromogens, for the examples of fluoran compounds, the following compounds can be exemplified.

3-diethylamino-6-methyl-7-anilinofluoran
3-dibutylamino-6-methyl-7-anilinofluoran
3-(N-ethyl-N-isobutylamino)-6-methyl-7-anilinofluoran
3-(N-methyl-N-propylamino)-6-methyl-7-anilinofluoran
3-(N-ethyl-N-isopentylamino)-6-methyl-7-anilinofluoran
3-diethylamino-7-(o-chloroanilino)fluoran
3-dibutylamino-7-(o-chloroanilino)fluoran
3-(N-ethyl-p-toluidino)-6-methyl-7-anilinofluoran
3-(N-cyclohexyl-N-methylamino)-6-methyl-7-anilinofluoran
3-pyrrolidino-6-methyl-7-anilinofluoran
3-piperidino-6-methyl-7-anilinofluoran
3-dimethylamino-7-(m-trifluoromethylanilino)fluoran
3-dipentylamino-6-methyl-7-anilinofluoran
3-(N-ethoxypropyl-N-ethylamino)-6-methyl-7-anilinofluoran
3-dibutylamino-7-(o-fluoroanilino)fluoran
3-diethylaminobenzo[a]fluoran
3-(N-ethyl-N-isobutylamino)-5,6-benzofluoran
3-dimethylamino-6-methyl-7-chlorofluoran
3-dimethylamino-5-methyl-7-dibenzylaminofluoran
3-diethylamino-7-dibenzylaminofluoran
3-diethylamino-5-chlorofluoran
3-diethylamino-6-(N,N-dibenzylamino)fluoran
3,6-dimethoxyfluoran, and the like.

Further, for the examples of near infrared absorbing chromogens, 3-(4-(4-(4-anilino)-anilino)anilino-6-methyl-7-chlorofluoran, 3,3-bis(2-(4-dimethylaminophenyl)-2-(4-methoxyphenyl)vinyl)-4,5,6,7-tetrachloro phthalide, 3,6,6'-tris(dimethylamino)spiro[fluorene-9,3'-phthalide] and the like can be exemplified.

Again, the compounds according to the present invention can be used together with other developers, and for the examples thereof, bisphenols, such as bisphenol A, 4,4'-sec-butylidene bisphenol, 4,4'-cyclohexylidene bisphenol, 2,2-dimethyl-3,3-bis(4-hydroxyphenyl)butane, 2,2'-dihydroxydiphenyl, pentamethylene-bis(4-hydroxybenzoate), 2,2-dimethyl-3,3-di(4-hydroxyphenyl) pentane, 2,2-di(4-hydroxyphenyl)hexane and the like; sulfur-containing bisphenols, such as 4,4'-dihydroxydiphenyl thioether, 1,7-di(4-hydroxyphenylthio)-3,5-dioxaheptane, 2,2'-bis(4-hydroxyphenylthio)diethyl ether, 4,4'-dihydroxy-3,3'-dimethylphenyl thioether and the like; 4-hydroxybenzoate esters, such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate, diphenylmethyl 4-hydroxybenzoate and the like; metal salts of benzoic acid, such as zinc benzoate and zinc 4-nitrobenzoate; salicylic acids, such as 4-(2-(4-methoxyphenyloxy)ethyloxy)salicylate; metal salts of salicylic acid, such as zinc salicylate; hydroxy sulfones, such as 4,4'-dihydroxydiphenyl sulfone, 2,4'-dihydroxydiphenyl sulfone, 4-hydroxy-4'-methyldiphenyl sulfone, 4-hydroxy-4'-isopropoxydiphenyl sulfone, 4-hydroxy-4'-butoxydiphenyl sulfone, 4,4'-dihydroxy-3,3'-diallyldiphenyl sulfone, 3,4-dihydroxy-4'-methyldiphenyl sulfone, and 4,4'-dihydroxy-3,3',5,5'-tetrabromodiphenyl sulfone; diesters of 4-hydroxyphthalic acid, such as dimethyl 4-hydroxyphthalate, dicyclohexyl 4-hydroxyphthalate and diphenyl 4-hydroxyphthalate; hydroxynaphthoate esters, such as 2-hydroxy-6-carboxynaphthalene; trihalomethyl sulfones, such as hydroxyacetophenone, p-phenylphenol, benzyl 4-hydroxyphenyl acetate, p-benzylphenol, hydroquinone-monobenzyl ether and trihalomethyl sulfones, such as tribromomethylphenyl sulfone; sulfonyl ureas, such as 4,4'-bis(p-toluenesulfonylaminocarbonylamino)diphenylmethane; and charge-transfer complex, such as tetracyanoquinodimethane and the like, can be exemplified.

The compounds according to the present invention can be used for carbonless papers according to the same manner as the ones for using known image-stabilizing agents, developers and sensitizers. For example, carbonless papers can be prepared by combining a paper sheet whereto a color-forming chromogen be applied, which is prepared by dispersing a color-forming chromogen encapsulated in microcapsules in an appropriate dispersing agent according to a publicly-known method and subsequently applying the said dispersion onto a paper, and another paper sheet whereto a developer be applied, which is prepared by applying suspension of the compound according to the present invention onto papers.

The compounds according to the present invention can be used for carbonless papers made in either forms of an unit-type structure, which comprises an upper-side paper wherein microcapsules encapsulating a coloring chromogen solution in an organic solvent being applied to the under surface of the paper and an under-side paper whereto a developer being applied onto the upper surface, or of so-called self-content paper, wherein both of said microcapsules and a developer being applied onto the same surface of the paper.

BEST MODE FOR CARRYING OUT THE INVENTION

Now, the present invention is further described in detail by referring to examples, however, it should be noted that the present invention shall not be limited to the scope described in the following examples.

EXAMPLE 1

Example for Synthesizing Compound 1-1

8.0 g of sodium hydroxide (0.20 mol) was dissolved in 100 ml of water, and 40.0 g (0.16 mol) of 4,4'-dihydroxy diphenyl sulfone (hereinafter referred to as BPS) was further added thereto. To the resulting solution, 100 ml of methyl isobutyl ketone (hereinafter referred to as MIBK) and further 7.0 g (0.04 mol) of dibromomethane were added, then the mixture was subjected to reflux under heating for 15 hours to take place the reaction. After the reaction, diluted-sulfuric acid was added to the reacted solution to adjust the water layer slightly acidic and to thereby separate said water layer. After washing the organic layer with 1% aqueous solution of NaOH to recover the unreacted BPS, MIBK was condensed and then cooled to thereby obtain 2.5 g of 1,1-bis[4-(4-hydroxyphenylsulfonyl)phenoxy]methane in white crystal state having a melting point of from 213° to 215° C. The purity of the obtained-compound determined by using high performance liquid chromatography was 95.2%, and the yield from dibromomethane was 12%.

EXAMPLE 2

Example for Synthesizing Compound 1-6

The reaction was taken place for 11 hours according to the same procedure described in the Example 1 except replacing bromomethane with 9.8 g (0.04 mol) of dibromohexane under reflux and heating. After the reaction, diluted-sulfuric acid was added to the reacted solution to adjust the water layer slightly acidic and to thereby separate said water layer. After washing the organic layer with 1% aqueous solution of NaOH to recover the unreacted BPS, MIBK was condensed and then removed, thereby affording 14.5 g of yellow-colored oil. According to an analysis by using high performance liquid chromatography, the content of the objective compound, 1,6-bis[4-(4-hydroxyphenylsulfonyl) phenoxy] hexane in the said oil was found to be 50.0%. The oil was further purified with column chromatography, thereby 3.5 g of the objective compound having a melting point of from 225° to 226° C. was obtained in white crystal state. The purity of the obtained-compound determined by using high performance liquid chromatography was 96.6%, and the yield from dibromohexane was 10%.

EXAMPLE 3

Example for Synthesizing Compound 1-25

The reaction was taken place for 2 hours according to the same procedure described in the Example 1 except replacing bromomethane with 5.0 g (0.04 mol) of 1,4-dichloro-2-butene under reflux and heating. After the reaction, diluted-sulfuric acid was added to the reacted solution to adjust the water layer slightly acidic and to thereby separate said water layer. After washing the organic layer with 1% aqueous solution of NaOH to recover the unreacted BPS, MIBK was condensed and cooled, thereby affording 5.9 g of 1,4-bis[4-(4-hydroxyphenylsulfonyl)phenoxy]-2-butene in white crystal state. According to an analysis by using high performance liquid chromatography, the purity of the objective compound was 91.7%, and the yield from 1,4-dichloro-2-butene was 27%.

Then, the objective compound obtained was further subjected to the recrystallization using methanol to separate the isomers. As a result, the cis-isomer was found to be amorphous, and the melting point of the trans-isomer was in a range of from 244° to 246° C.

EXAMPLE 4

Example for Synthesizing Compound 1-30

To 200 ml of dehydrated-dimethylformamide, 27.2 g (0.08 mol) of 4-benzyloxy-4'-hydroxydiphenyl sulfone was dissolved, and 3.5 g (0.088 mol) of 60% oily sodium hydride was further added thereto. After adding 5.7 g (0.04 mol) of bis(2-chloroethyl)ether further, then the mixture was allowed to a reaction for 4 hours at 10° C. After the reaction, 200 ml of MIBK and 200 ml of water are added to separate the water layer while maintaining temperature at 70° C. The MIBK layer was then cooled to afford 23.7 g of 2,2'-bis[4-(4-benzyloxyphenylsulfonyl) phenoxy]diethyl ether in white crystal state. The yield from bis(2-chloroethyl)ether was 79%.

23.7 g of the crystals obtained was further added to a mixed solution composed of 80 ml of hydrobromic acid and 80 ml of acetic acid, then the solution was allowed to a reaction for 30 min. under reflux and heating. After the reaction, the solvent therein was taken out under reduced pressure, and the reacted-product was subsequently added with 100 ml of methanol following by crystallization, filtration and drying, thereby affording 11.4 g of the objective compound, 2,2'-bis[4-(-hydroxyphenylsulfonyl)phenoxy] diethyl ether in white crystal state, of which melting point being a range of from 171° to 172° C. According to an analysis by using high performance liquid chromatography, the purity of the objective compound was 98.7%, and the yield from bis(2-chloroethyl)ether was 50%.

EXAMPLE 5

Preparation of Thermal Recording Papers

| Dispersed solution of Coloring Chromogen (A solution) | |
|---|---|
| 2-anilino-3-methyl-6-dibutylaminofluoran | 7.0 g |
| Polyvinyl alcohol 15% aqueous solution | 30.0 g |
| Filler (calcium carbonate) | 13.5 g |
| Pure water | 49.5 g |
| Dispersed solution of Developer (B solution) | |
| The compound of the present invention | 7.0 g |
| Polyvinyl alcohol 15% aqueous solution | 30.0 g |
| Filler (calcium carbonate) | 13.5 g |
| Pure water | 49.5 g |
| Dispersed solution of Filler (C solution) | |
| Polyvinyl alcohol 15% aqueous solution | 30.0 g |
| Filler (calcium carbonate) | 20.5 g |
| Pure water | 49.5 g |

The components of each solution described above were thoroughly grinded by using a sand grinder to prepare A, B and C solutions, respectively. By mixing 1 part by weight of A solution, 2 parts by weight of B solution and 1 part by weight of C solution, a coating solution was prepared. After applying the coating solution onto plain papers by using wire rod (No. 12) and then dried them, the papers applied were subjected to calendering to prepare thermal recording papers.

Comparison Example 1

Recording papers were prepared according to the same procedure described in the Example 5, except replacing the compound of the present invention with 4-hydroxy-4'-isopropoxydiphenyl sulfone.

Comparison Example 2

Recording papers were prepared according to the same procedure described in the Example 5, except replacing the compound of the present invention with 1,3-bis-(4-hydroxydiphenylsulfone-4'-yloxy)-2-propanol which is disclosed in Japanese Patent Laid-opened No. Hei 5-194368.

EXAMPLE 6

Test on Resistance of Recording Papers to Plasticizers

Each of the recording papers prepared in the Example 5 and the Comparison Examples was subjected to color developing in checkered pattern at a printing voltage of 26 V and a pulse width of 1.8 ms by using a test apparatus for developing color on thermal recording paper (manufactured by Okura Denki, Type: TH-PMD), and the colored-images on the paper were tightly sealed with rapping film made of vinyl chloride. The sealed-paper was kept for 8 hours at 40° C. to determine the resistance to plasticizers. Colored-density before and after the test was measured by using Macbeth reflection densitometer RD-514 (filter used: # 106). The results are shown in Table 5.

TABLE 5

| Compound used for thermal recording paper | Colored-image area | |
|---|---|---|
| | Color density measured before starting test | Color density measured after applied to test (Remaining Rate of Color) |
| Compound 1-1 | 1.03 | 0.78 (76%) |
| Compound 1-6 | 1.08 | 0.70 (65%) |
| Compound 1-28 | 1.08 | 0.82 (75%) |
| Compound 1-30 | 1.10 | 0.88 (82%) |
| Compound 1-35 | 1.08 | 0.71 (67%) |
| Comparison Example 1 | 1.16 | 0.07 (6%) |
| Comparison Example 2 | 0.88 | 0.81 (92%) |

In the table above, the greater values means stronger density of the colored-images. And greater values in the remaining rate of color means less fading of color. In the table shown above, it is demonstrated that the thermal recording papers using the compounds of the present invention as a developer have improved the resistance of colored-images to plasticizers. The remaining rate of color was calculated into percentage by dividing the color density measured after test by the one before test.

EXAMPLE 7

Test on Resistance of Thermal Recording Papers to Moisture and Heat

Each of the thermal recording papers prepared in the Example 5 and Comparison Examples were allowed to stand for 2 hours at an atmosphere of 50° C. and 80% R.H. Then, the density on background was measured by using Macbeth reflection densitometer RD-514 (filter used: # 106). The results are shown in Table 6.

TABLE 6

| Compound used for thermal recording paper | Background Area | |
|---|---|---|
| | Color density measured before starting test | Color density measured after applied to test |
| Compound 1-1 | 0.07 | 0.07 |
| Compound 1-6 | 0.05 | 0.06 |
| Compound 1-28 | 0.05 | 0.05 |
| Compound 1-30 | 0.05 | 0.06 |
| Compound 1-35 | 0.06 | 0.06 |

TABLE 6-continued

| Compound used for thermal recording paper | Background Area | |
|---|---|---|
| | Color density measured before starting test | Color density measured after applied to test |
| Comparison Example 1 | 0.06 | 0.06 |
| Comparison Example 2 | 0.07 | 0.15 |

The greater values in the table above means stronger color density on the background. Consequently, it is demonstrated in the table above that the recording papers using the compound of the present invention as a developer can provide excellent resistance property against moisture and heat to the background.

INDUSTRIAL USE OF THE INVENTION

In the field of recording materials, material preservability including resistances to plasticizers and oils is a highly important property. The diphenyl sulfone derivatives according to the present invention shall be found as excellent materials since those are improved in such preservability. In particular, when the compounds are used as a developer, those can provide recording materials which can provide enough sensitivity in coloring of recording materials, excellent preservability of background in resistance tests to moisture and heat and good resistance to plasticizers.

Further, the diphenyl sulfone derivatives of the present invention can be also used for an image-stabilizing agent having excellent preservability.

What is claimed is:

1. A recording material comprising:

a coloring chromogen; and at least one diphenyl sulfone derivative represented by formula (I)

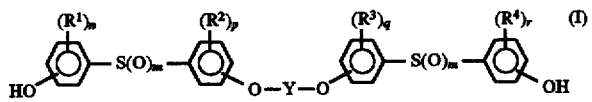

wherein Y represents a linear or branched, saturated or unsaturated $C_1$–$C_{12}$ hydrocarbon group, a $C_1$–$C_8$ hydrocarbon group having an ether linkage, or a group represented by a formula

wherein R represents methylene or ethylene; $R^1$, $R^2$, $R^3$ and $R^4$ each independently represent lower alkyl or lower alkenyl; m represents 0 or an integer of 1 or 2; and n, p, q and r each independently represent 0 or an integer of 1 to 4, provided that when n, p, q and r are each 2 or above the substituents represented by $R^1$, $R^2$, $R^3$ and $R^4$ may each be different.

2. A recording material comprising:

a coloring chromogen; and at least one diphenyl sulfone derivative represented by formula (II)

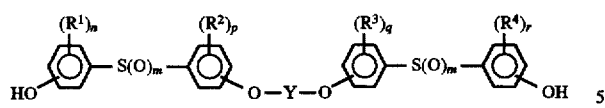

wherein Y represents a linear or branched, saturated or unsaturated $C_1$–$C_{12}$ hydrocarbon group, a $C_1$–$C_8$ hydrocarbon group having an ether linkage, or a group represented by a formula

wherein R represents methylene or ethylene; $R^1$, $R^2$, $R^3$ and $R^4$ each independently represent lower alkyl or lower alkenyl; m represents 0 or an integer of 1 or 2; and n, p, q and r each independently represent 0 or an integer of 1 to 4, provided that when n, p, q and r are each 2 or above the substituents represented by $R^1$, $R^2$, $R^3$ and $R^4$ may each be different.

* * * * *

UNITED STATES PATENT AND TRADEMARK OFFICE
CERTIFICATE OF CORRECTION

PATENT NO. : 5,801,288
DATED : September 1, 1998
INVENTOR(S) : Hiroshi Fujii, et al.

It is certified that error appears in the above-identified patent and that said Letters Patent is hereby corrected as shown below:

On Title Page, city of residence of inventor Ryuichi Kaneko should be TOKYO.

In Column 12, the last formula in the column should read as follows:

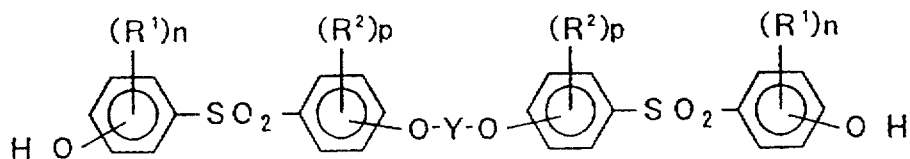

In Column 21, the formula should read as follows:

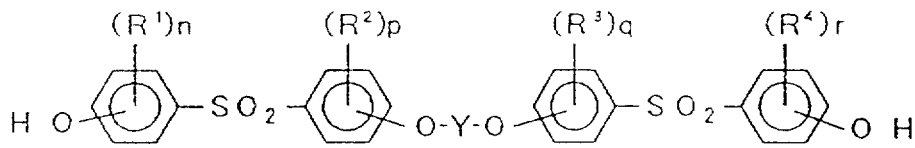

Signed and Sealed this

Sixteenth Day of February, 1999

Attest:

Attesting Officer

Acting Commissioner of Patents and Trademarks